United States Patent
Imazu et al.

(10) Patent No.: US 9,279,760 B2
(45) Date of Patent: Mar. 8, 2016

(54) ANALYZER AND AGITATING APPARATUS

(71) Applicants: Masanori Imazu, Takasago (JP); Masato Kusuda, Kobe (JP)

(72) Inventors: Masanori Imazu, Takasago (JP); Masato Kusuda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 126 days.

(21) Appl. No.: 14/012,509

(22) Filed: Aug. 28, 2013

(65) Prior Publication Data

US 2014/0065018 A1    Mar. 6, 2014

(30) Foreign Application Priority Data

Aug. 30, 2012  (JP) ................................ 2012-190358

(51) Int. Cl.
  *G01N 21/01*  (2006.01)
  *G01N 35/04*  (2006.01)
  *B01F 11/00*  (2006.01)
  *G01N 35/00*  (2006.01)

(52) U.S. Cl.
  CPC ............ *G01N 21/01* (2013.01); *B01F 11/0028* (2013.01); *G01N 35/04* (2013.01); *G01N 2035/00524* (2013.01)

(58) Field of Classification Search
  None
  See application file for complete search history.

(56) References Cited

U.S. PATENT DOCUMENTS

| | | | |
|---|---|---|---|
| 5,642,938 A * | 7/1997 | Nakagawa et al. | 366/110 |
| 2007/0110617 A1* | 5/2007 | Nagai et al. | 422/65 |
| 2007/0110627 A1* | 5/2007 | Nagai et al. | 422/99 |
| 2009/0009757 A1* | 1/2009 | Mototsu et al. | 356/246 |
| 2010/0111767 A1* | 5/2010 | Yonekura et al. | 422/65 |
| 2011/0086432 A1* | 4/2011 | Herz et al. | 436/174 |

* cited by examiner

*Primary Examiner* — Jill Warden
*Assistant Examiner* — Benjamin Whatley
(74) *Attorney, Agent, or Firm* — Sughrue Mion, PLLC (57) ABSTRACT

An analyzer comprises a container supplying unit which supplies a container, an agitating unit which agitates liquid in the container, and a measurement unit which performs a measurement using the liquid agitated by the agitating unit. The agitating unit comprises a base which is configured to move relative to the container supplying unit, a driving source which is mounted on the base, a container catcher which is configured to catch the container at one side, a transmitting member which transmits the power of the driving source to the other end side of the container catcher, and a supporting member which supports the container catcher at a position between one end and the other end of the container catcher.

13 Claims, 11 Drawing Sheets

ANALYZER AND AGITATING APPARATUS

FIELD OF THE INVENTION

The present invention relates to an agitation apparatus for agitating a liquid in a container, and an analyzer provided with same.

BACKGROUND

Sample analyzers used in the fields of biochemistry, immunology, coagulation and the like, dispense reagent and sample into a reaction container and mix the reagent and the sample by agitating the liquid within the reaction container to prepare a measurement sample to be used for measurements.

United States Patent Application Publication No. 2011/0086432 discloses a mixing apparatus provided with a cuvette holder for holding a cuvette, a transport arm for moving the cuvette holder, a rubber disk disposed between the transport arm and the cuvette holder, an oscillating device including a motor, and an eccentric pin provided on the motor. The cuvette holder has a connector hole formed complementarily with the eccentric pin. The motor is fixed on a base at a predetermined position, and the transport arm is movable relative to the base. When mixing the sample within the cuvette, the transport arm is moved so that the connector hole of the cuvette holder is lowered onto the eccentric pin to connect the connector hole and the eccentric pin. The cuvette holder is oscillated by circular motion of the eccentric pin when the motor shaft is rotated, thus mixing the sample within the cuvette.

When the cuvette holder holds a cuvette in this mixing apparatus, the transport arm is moved to move the cuvette holder that does not hold a cuvette to a cuvette supplying position since a cuvette must be held in the cuvette holder. When sample or reagent is dispensed to the cuvette held in the cuvette holder, the transport arm must be moved to transfer the cuvette holder to the sample or reagent dispensing position so as to dispense the sample or reagent to the cuvette. However, it is difficult to ensure positional accuracy of the cuvette holder since the cuvette holder is supported on the transport arm only by the flexible rubber disk, hence concern that the cuvette will be inadequately supported in the cuvette holder.

SUMMARY OF THE INVENTION

The scope of the present invention is defined solely by the appended claims, and is not affected to any degree by the statements within this summary.

A first aspect of the present invention is an analyzer comprising: a container supplying unit which supplies a container; an agitating unit which agitates liquid in the container; and a measurement unit which performs a measurement using the liquid agitated by the agitating unit. The agitating unit comprises: a base which is configured to move relative to the container supplying unit; a driving source which is mounted on the base; a container catcher which is configured to catch the container at one side; and a transmitting member which transmits the power of the driving source to the other end side of the container catcher.

A second aspect of the present invention is an analyzer comprising: a container supplying unit which supplies a container; an agitating unit which agitates liquid in the container; and a measurement unit which performs a measurement using the liquid agitated by the agitating unit. The agitating unit comprises: a base which is configured to move relative to the container supplying unit; a driving source which is mounted on the base; a container catcher which is configured to catch the container at one side; and a rotating shaft which transmits the power of the driving source to the other end side of the container catcher and oscillates the container catcher. The rotating shaft is rotated by the driving source, and passes through the other end of the container catcher.

A third aspect of the present invention is an agitating apparatus for agitating a liquid in a container, comprising: a base which is configured to be movable; a driving source which is mounted on the base; a container catcher which is configured to catch the container at one side; a transmitting member which transmits the power of the driving source to the other end side of the container catcher and oscillates the container catcher; and a supporting member which supports the container catcher at a position between one end and the other end of the container catcher.

DETAILED DESCRIPTION OF THE PREFERRED EMBODIMENTS

The preferred embodiments of the present invention will be described hereinafter with reference to the drawings.
[Structure of the Sample Analyzer]

Figure 1:
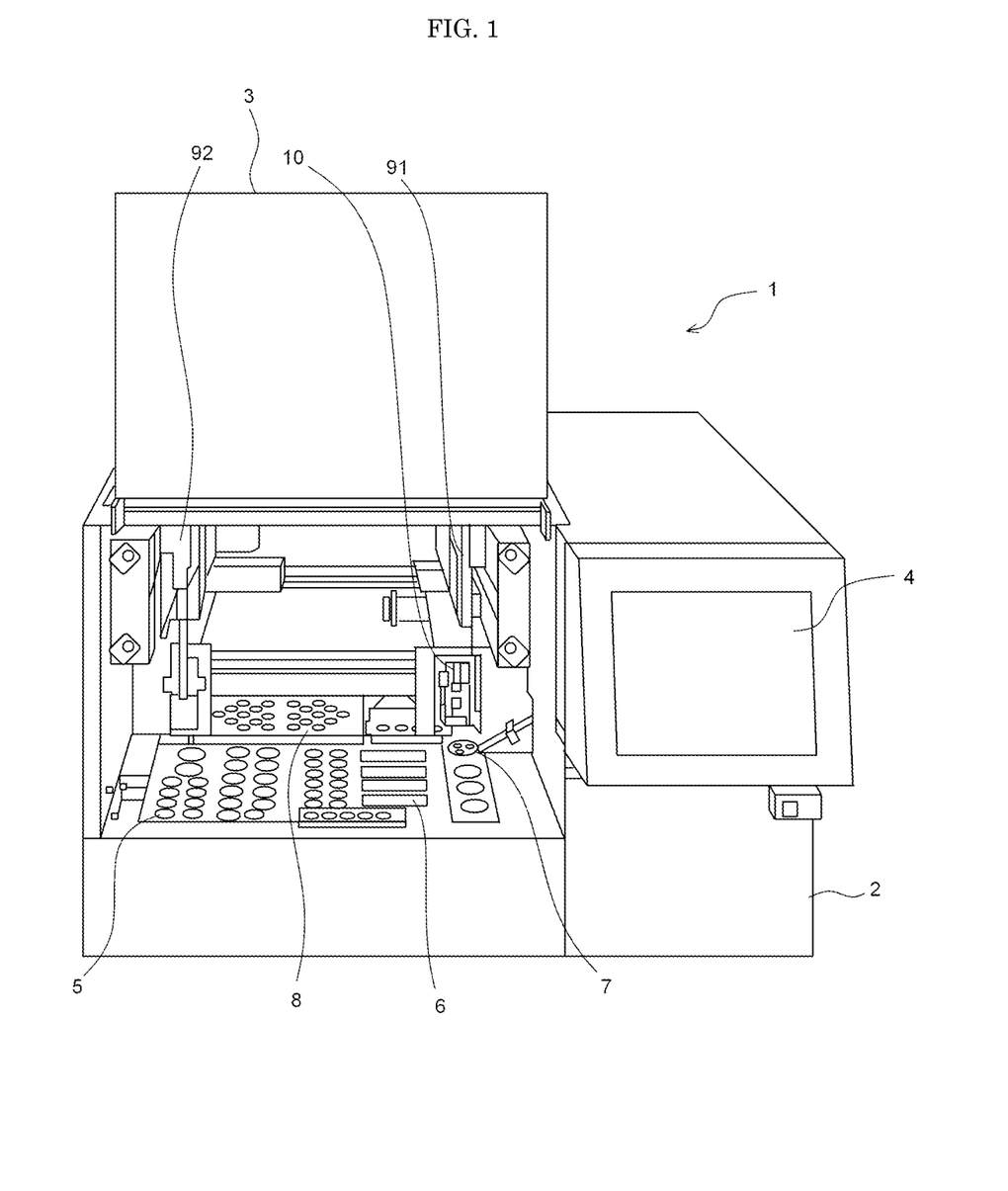
FIG. 1 shows the structure of an embodiment of the sample analyzer.

FIG. 1 shows the structure of an embodiment of the sample analyzer. FIG. 1 shows the sample analyzer 1 viewed from above at a frontal elevation. The sample analyzer 1 of the embodiment performs analysis by optically measuring the degree of activity or the amount of a specific substance related to coagulation and fibrinolytic function of a sample (blood sample). The sample analyzer 1 optically measures a sample using coagulation time, synthetic substrate, and immunoturbidimetric assay methods. Coagulation time method measurement items include PT (prothrombin time), APTT (active partial thromboplastin time), FbG (fibrinogen concentration) and the like. Measurement items of the synthetic substrate method include AT and the like, and measurement items of the immunoturbidimetric assay method include D-dimer, FDP and the like.

The sample analyzer 1 has an apparatus body 2, and a cover 3 which covers from the top surface to the front surface. The cover 3 is connected to the apparatus body 2 by a hinge so as to be capable of opening and closing. The sample analyzer 1 has a touch panel display 4; a user inputs information (for example, sample ID, patient information, measurement start instruction) required for analyzing a sample using the touch screen display, and the touch screen display 4 also shows measurement results.

The part of the apparatus body 2 that is covered by the cover 3 when the cover 3 is closed forms an open area. This open area is provided with a reagent section 5 for installing measurement reagent, primary dispensing container section 6 for installing containers into which sample are dispensed, reaction container supplier 7 for supplying reaction containers for mixing and reacting reagent and sample, and measuring unit 8 for measuring a sample in a reaction container disposed on the same table. A sample dispensing unit 91 for dispensing sample, reagent dispensing unit 92 for dispensing reagent and container transport unit 10 for moving the reaction container from the reaction container supplier 7 to the measuring unit 8 are also provided on the table.

The reagent section 5 has a plurality of holes for accommodating reagent containers. The reagent section 5 has a built in cooling device capable of cooling the accommodated reagent containers at a constant temperature.

The primary dispensing container for dispensing sample can be installed in and detached from the primary dispensing container section 6. The primary dispensing container has a plurality of concavities into which sample is dispensed by the sample dispensing unit 91. In the sample analyzer of the present embodiment, measurement instructions for a plurality of measurement items may be issued for a single sample. In such cases the same number of reaction containers are prepared as the specified measurement items, and sample must be dispensed to each respective reaction container. The primary dispensing container section 6 dispenses a single sample to a single concavity of the primary dispensing container using the sample dispensing unit 91 to aspirate sample from a collection tube accommodating the sample. The sample dispensed in a single concavity is then dispensed by the sample dispensing unit 91 to one or more reaction containers according to the measurement item.

The reaction container supplier 7 accommodates a plurality of reaction containers and supplies (ejects) the accommodated reaction containers one by one.

The measuring unit 8 has a plurality of holes for holding reaction containers. The reaction containers that contain sample and reagent are transported by the container transporting unit 10 and are held in the holes of the measuring unit 8. A heater is provided within the measuring unit 8, and this heater heats the liquid in the reaction container disposed in each of the holes to a constant temperature. A light emitting part and a light receiving part are provided at each hole of the measuring unit 8, and the degree of light absorbency of the measurement sample (the mixture of sample and reagent) in the reaction container of each hole can be measured. The measured data are transmitted to a controller built into the apparatus body 2, the received data are process by the controller and measurement results are obtained.

Guide rails extend in the front-to-back direction and lateral direction in the apparatus body 2, and the sample dispensing unit 91 and reagent dispensing unit 92 are respectively movable along the guide rails in the front-to-back and lateral directions, that is, movable in the two perpendicular horizontal axial directions. The sample dispensing unit 91 and the reagent dispensing unit 92 are each provided with a nozzle for dispensing sample and reagent. Each nozzle is movable in vertical directions, and the nozzle is disposed in the upward position when the sample dispensing unit 91 and reagent dispensing unit 92 are moving, and the nozzle is lowered when sample and reagent are discharged from the sample dispensing unit 91 and reagent dispensing unit 92.

The container transporting unit 10 is movable in lateral directions along guide rails provided within the apparatus body 2. The container transporting unit 10 grips the reaction container supplied from the reaction container supplier 7, and moves the reaction container to a hole in the measuring unit 8. The container transporting unit 10 oscillates the held reaction container to agitate the sample and reagent within the reaction container.

In the sample analyzer 1 of the present embodiment, sample aspirated from the collection tube by the sample dispensing unit 91 is dispensed (primary dispensation) at a fixed dose into a hole of the primary dispensing container installed in the primary dispensing container section 6. On the other hand, the reaction container supplied from the reaction container supplier 7 is gripped by the container transporting unit 10. Part of the sample in the holes of the primary dispensing container is aspirated by the sample dispensing unit 91 and dispensed (secondary dispensation) to the reaction container held in the container transporting unit 10. The reaction container holding the sample of the secondary dispensation is moved to the holder of the measuring unit 8 by the container transporting unit 10 and heated for a predetermined time while in the holder. After the predetermined heating time, the heated reaction container is removed from the measuring unit by the container transporting unit 10. Blood coagulation reagent corresponding to a measurement item is aspirated by the reagent dispensing unit 92 from the reagent container in the reagent section 5, and dispensed to the reaction container held in the container transporting unit 10. The container transporting unit 10 then oscillates the reaction container to agitate and mix the sample and reagent within the reaction container to prepare a measurement sample. The reaction container that has been agitated to mix the sample and reagent contained therein is then returned to the holder of the measuring unit 8 and again heated for a predetermined time. The sample and blood coagulation reagent are thus mixed within the reaction container and the blood coagulation reaction occurs. In the measuring unit 8, the sample measurements are performed by irradiating light on the reaction container that accommodates the measurement sample, and detecting the amount of light transmitted through the container.

Structure of the Container Transporting Unit

Figure 2:
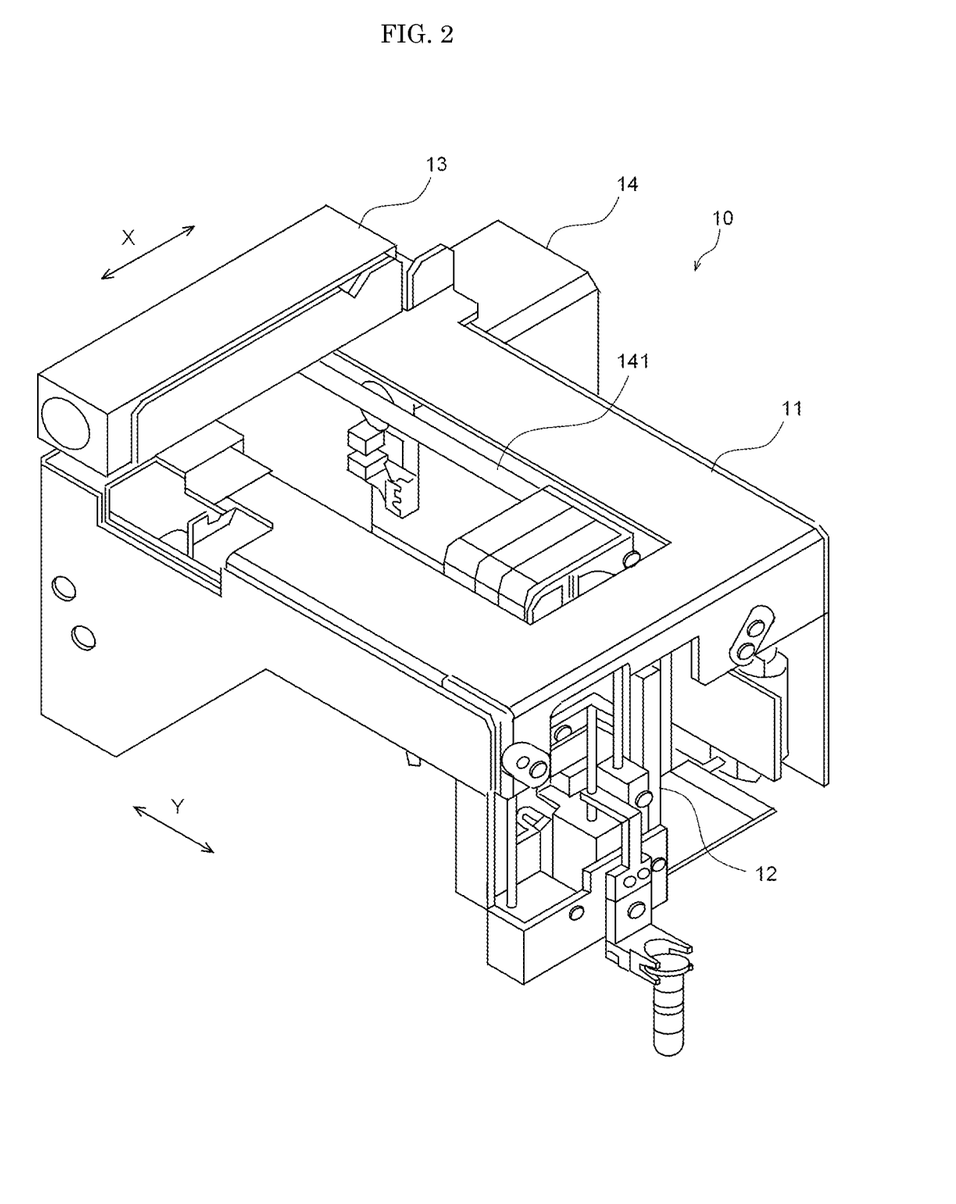
FIG. 2 is a perspective view showing the structure of a container transporting unit.

The structure of the container transporting unit is described in detail below. FIG. 2 is a perspective view showing the structure of the container transporting unit. The container transporting unit 10 has a frame 11, and an agitating apparatus 12 mounted within the frame 11. The frame 11 is a metal plate which is curved in a boxy shape that is open below so as to cover the agitating apparatus 12 from above. A guide part 13 which has a guide rail passing through is provided above the frame 11. The frame 11 is connected to the transmission belt of the apparatus body 2, and the transporting unit 10 is moved laterally (X direction in the drawing) when the transmission belt is driven and the guide part 13 slides on the guide rail.

The agitating apparatus 12 is movable in the front-to-back direction, that is, the Y direction, within the frame 11. A motor 14 for moving the agitating apparatus 12 is provided on the outside of the frame 11. Also provided inside the frame 11 are guide rail 141 extending in the front-to-back direction, and a drive force transmission mechanism which includes a transmission belt and pulley. The agitating apparatus 12 has a guide part through which a guide rail 141 passes; actuation of the motor 14 drives the power transmission mechanism to move the agitating apparatus 12 when the guide part slide son the guide rail 141. The agitating apparatus 12 is thus freely movable in the X direction and the Y direction within a range of movement.

Figure 3:
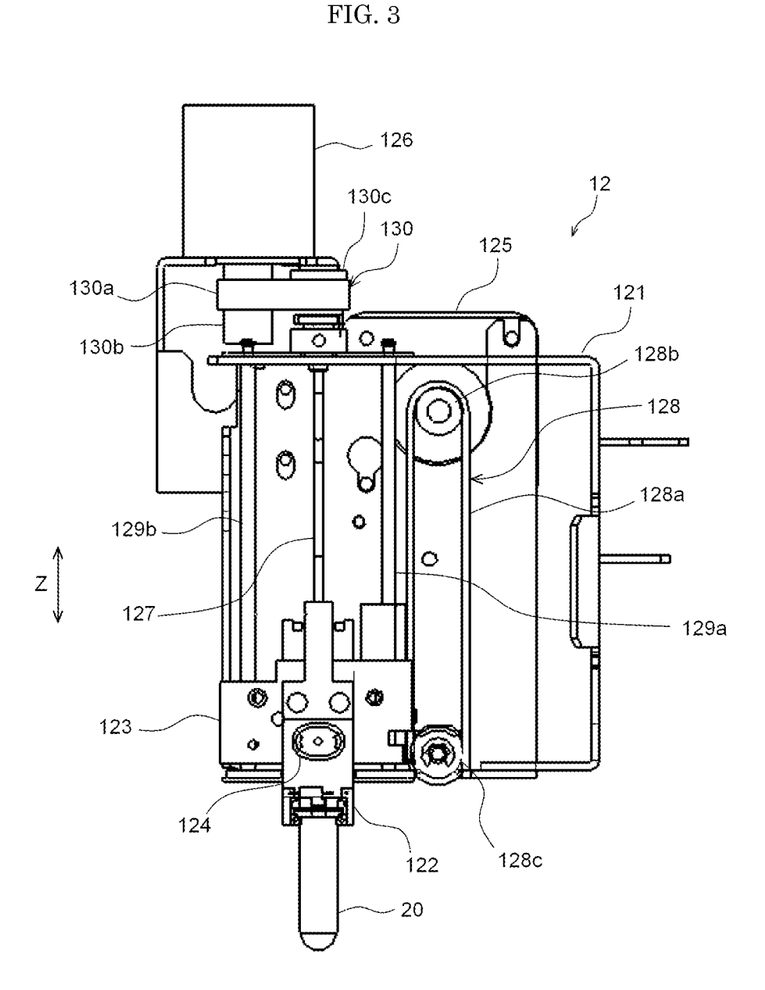
FIG. 3 is a front view showing the structure of agitation apparatus of the embodiment.
Figure 4:
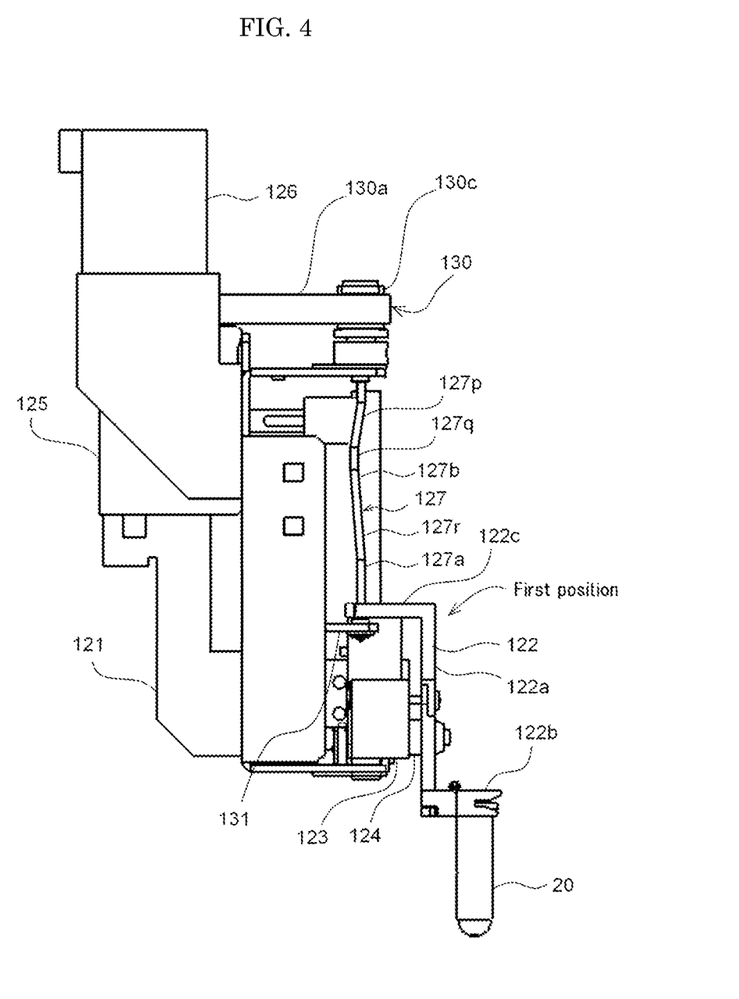
FIG. 4 is a left side view showing the structure of agitation apparatus of the embodiment.

FIG. 3 is a frontal view showing the structure of the agitating apparatus, and FIG. 4 is a left side view of same. The agitating apparatus 12 of the present embodiment is provided with a base 121, a catcher 122 which holds the reaction container, an elevator block 123, rubber support 124 which connects the elevator block 123 and the catcher 122, a motor 125 which moves the elevator block 123 and the catcher 122 in vertical directions (Z directions in the drawing), a motor 126 which oscillates the reaction container held by the catcher 122, and a rotating shaft 127 which is connected to the output shaft of the motor 126.

The base 121 is formed by a curved metal plate into the basic skeletal structure of the agitating apparatus 12. A motor 125 is mounted on the base 121 to move the catcher 122 in vertical directions. A power transmission mechanism 128, which includes a transmission belt 128a and pulleys 128b and 128c, is connected to the output shaft of the motor 125, and an elevator block 123 is connected to the transmission belt 128a of the power transmission mechanism 128. A through hole is provided in the elevator block 123, and guide rails 129a and 129b, which extend from the top part to the bottom part of the base 121, pass through this through hole in the elevator block 123. When the motor 125 is operating, the power transmission mechanism 128 is actuated to move the elevator block 123 in vertical directions as the elevator block 123 slides on the guide rails 129a and 129b.

The rubber support 124 is mounted on the front surface of the elevator block 123, and this rubber support 124 supports the catcher 122. The rubber support 124 is elastic, and therefore the catcher 122 is connected so as to be displaceable (oscillatable) within a predetermined range (that is, a range allowed by the rubber elasticity of the rubber support 124) relative to the elevator block 123.

The catcher 122 is configured mainly by synthetic resin such as polyacetal or the like, and has a plate-like base part 122a which extends in vertical directions, a gripping part 122b provided at the bottom end of the base part 122a, and a substantially horizontal plate-like connecting part 122c provided at the top end of the base part 122a. The rubber support 124 mentioned above is connected to the base part 122a. The gripping part 122b is the part that holds the reaction container.

Figure 5:
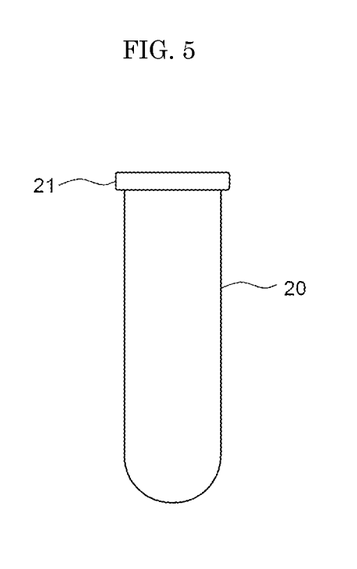
FIG. 5 is a front view showing the structure of a reaction container.

The structure of the reaction container is described below. FIG. 5 is a frontal view showing the structure of the reaction container. The reaction container 20 is cylindrical in shape with a semi-spherical bottom part. An empty space is provided inside the reaction container to accommodate sample and reagent. An annular flange collar 21 is provided at the top end of the reaction container 20.

The agitating apparatus 12 is described below using FIGS. 3 and 4. The gripping part 122b protrudes forward from the bottom end of the base part 122a. The gripping part 122b has a structure and shape which is capable of engaging the flange collar 21 of the reaction container 20.

The connecting part 122c extends backward from the top end of the base part 122a. A through hole is provided in the connecting part 122c, and the reaction container 20 is oscillatable via this through hole in a manner to be described later.

A motor 126 (step motor) is mounted on the top end of the base 121. The output shaft of the motor 126 extends downward and is connected to a power transmission mechanism 130 which includes a transmission belt 130a. and pulleys 130b and 130c. A rotating shaft 127 is connected to the driven pulley 130c of the power transmission mechanism 130. The rotating shaft 127 is a metal rod extending from the top end of the base 121 to a bearing 131 provided therebelow. The top end and the bottom end of the rotating shaft 127 are linear shaped parts along the center of rotation of the rotating shaft 127. The linear part on the bottom side specifically is a positioning part 127a which supports the catcher 122 when the catcher holds a reaction container 20. The intermediate part of the rotating shaft 127 is an eccentric part 127b which is curved so as to depart from the center of rotation of the rotating shaft 127. The eccentric part 127b has a first incline 127p at the top side, a linear part 127q at the intermediate part, and a second incline 127r at the bottom side. The first incline 127p extends to the linear part on the top end side of the rotating shaft 127, and is inclined so as to increase the amount of displacement from the center of rotation of the rotating shaft downward. The first incline 127p extends to the linear part 127q at the bottom end to maximize the amount of displacement from the center of rotation. The linear part 127q extends parallel to the axial direction of the center or rotation. The second incline 127r extends to the linear part on the bottom end side of the rotating shaft 127, and is inclined so as to decrease the amount of displacement from the center of rotation of the rotating shaft downward. The top end of the second incline 127r extends the bottom end of the linear part 127q. The angle of inclination of the second incline 127r (that is, the angle formed in the axial direction of the second incline 127r relative to the axial direction of the center of rotation of the rotating shaft 127) is less than the angle of inclination of the first incline 127p (that is, the angle formed by the axial direction of the first incline 127p relative to the axial direction of the center of rotation of the rotating shaft 127).

The rotating shaft 127 passes through the previously mentioned through hole in the connecting part 122c of the catcher 122. The size of the through hole is slightly larger than the diameter of the rotating shaft 127. Therefore, the connecting part 122c is movable from the positioning part 127a through the second incline 127r toward the linear part 127q.

Operation of the Agitating Apparatus

The operation of the agitating apparatus of the present embodiment is described below. When the reaction container 20 is supplied from the reaction container supplier 7, the motor 125 is actuated in the agitating apparatus 12 to position the connecting part 122c of the catcher 122 at the positioning part 127a of the rotating shaft 127. Hence, the elevator Nock 123 and the catcher 122 integratedly descend as a unit, and the connecting part 122c moves along the rotating shaft 127 toward the positioning part 127a. The catcher 122 therefore is disposed at the first position shown in FIGS. 3 and 4 (refer to the dashed line in FIG. 7).

When the catcher 122 is disposed at the first position and the rotating shaft 127 is rotated by the motor 126, the position of the positioning part 127a is unchanged relative to the center of rotation because the positioning part 127a is provided along the center of rotation. That is, the position of the positioning part 127a does not change relative to the base 121 whatever the position of the eccentric part 127b of the rotational shaft 127 relative to the center of rotation. Therefore, when the catcher 122 is disposed at the first position (that is, when the catcher 122 is supported by the positioning part 127a), the position (orientation) relative to the base 121 of the catcher 122 remains constant.

At this time the catcher 122 is supported at two points by the rubber support 124 and the rotating shaft 127. Any reduction of positional accuracy of the catcher 122 is inhibited by the elasticity of the rubber support 124 so as to ensure excellent positional integrity.

In this condition, the container transporting unit 10 is moved in the X direction and the Y direction to move the catcher 122 toward the reaction container supplier 7. The catcher 122 is positioned so that the gripping part 122b is behind the reaction container 20, and the motor 14 is then actuated to move the agitating apparatus 12 forward within the frame 11. The gripping part 122b thus engages the flange 21 of the reaction container 20. When the catcher 122 grips the flange 21 of the reaction container 20, the motor 125 is actuated to integratedly raise the elevator block 123 and the catcher 122 as a unit. The reaction container 20 is thus removed from the reaction container supplier 7.

Figure 6:
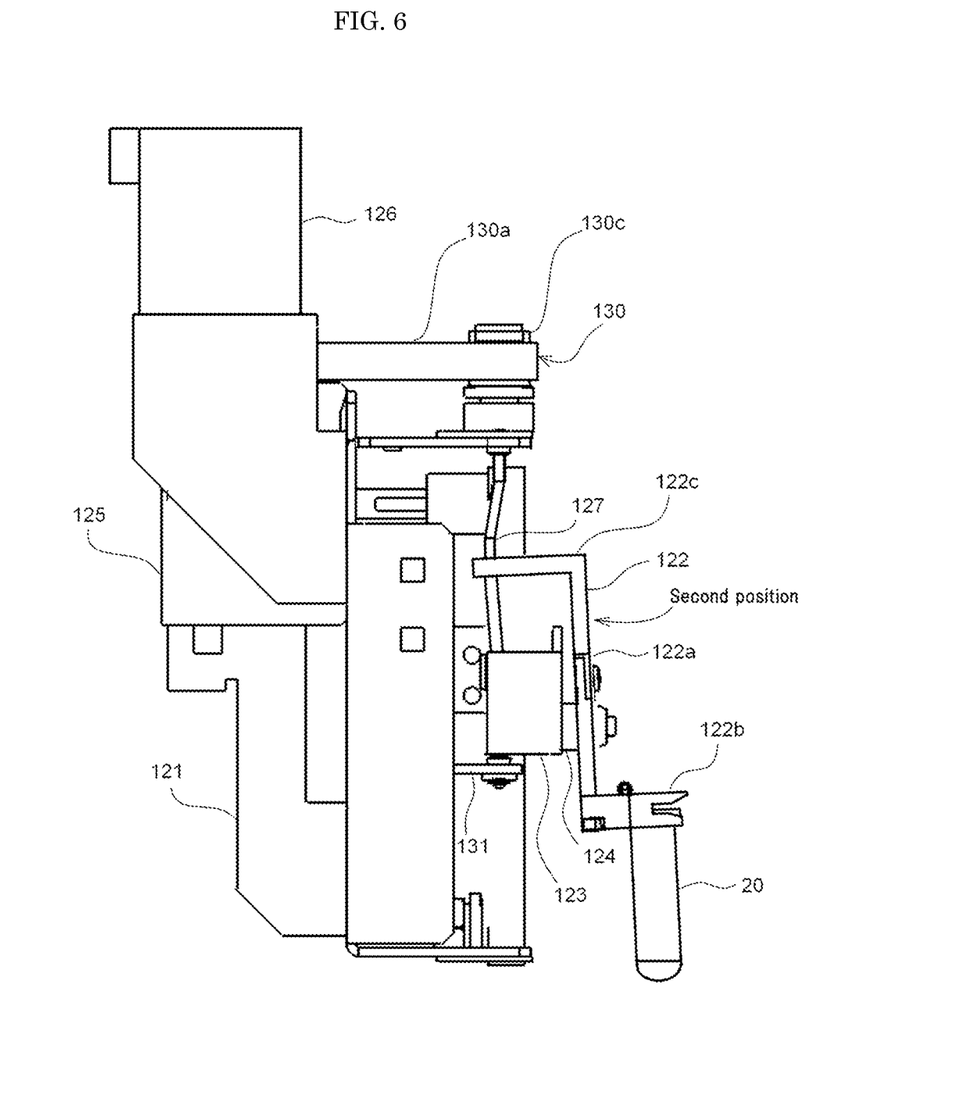
FIG. 6 is a left side view showing the structure of the agitation apparatus when the catcher is elevated.

FIG. 6 is a left side view showing the structure of the agitating apparatus when the catcher 122 is elevated; When the elevator block 123 and the catcher 122 are raised via the drive of the motor 125, the connecting part 122c of the catcher 122 is positioned on the linear part 127q of the rotating shaft 127. The catcher 122 is therefore set at the second position shown in FIG. 6.

When a sample is to be dispensed to the reaction container and the catcher 122 holds the reaction container 20 at the second position, the container transporting unit 10 is moved in the X direction and the Y direction to dispose the catcher 122 at the sample dispensing position to receive the sample. When the catcher 122 is disposed at the sample dispensing position, the sample dispensing unit 91 aspirates the sample from the primary dispensing container and dispenses this sample into the reaction container held by the catcher 122. When the sample has been thus dispensed to the reaction container 20, the container transporting unit 10 is moved in the X direction and the Y direction to move the catcher 122 to the measuring unit 8. With the catcher 122 positioned above one holder of the measuring unit 8, the motor 125 is actuated and the elevator block 123 and the catcher 122 integratedly descend as a unit so that the reaction container 20 is inserted into the hole. After the reaction container 20 is inserted in the holder, the motor 14 is actuated to move backward within the frame 11. The gripping part 122b and the flange 21 of the reaction container 20 thus disengage and the reaction container 20 is removed from the catcher 122.

When dispensing the reagent into the reaction container, the container transporting unit 10 is moved in the X direction and the Y direction to move the catcher 122 toward the measuring unit 8. The catcher 122 is positioned behind the reaction container 20 held in the holder of the measuring unit 8, and the motor 14 is then actuated to move the agitating apparatus 12 forward within the frame 11. The gripping part 122b thus engages the flange 21 of the reaction container 20. When the catcher 122 grips the flange 21 of the reaction container 20, the motor 125 is actuated to integratedly raise the elevator block 123 and the catcher 122 as a unit. The reaction container 20 is thus removed from the holder of the measuring unit 8.

When the catcher 122 holds the reaction container 20 at the second position, the container transporting unit 10 is moved in the X direction and the Y direction to dispose the catcher 122 at the reagent dispensing position to receive the reagent. When the catcher 122 is disposed at the reagent dispensing position, the reagent dispensing unit 92 aspirates the reagent from the reagent container and dispenses this reagent into the reaction container 20 held by the catcher 122. When the reagent is thus dispensed into the reaction container 20, the agitating apparatus 12 performs the agitation operation.

Figure 7:
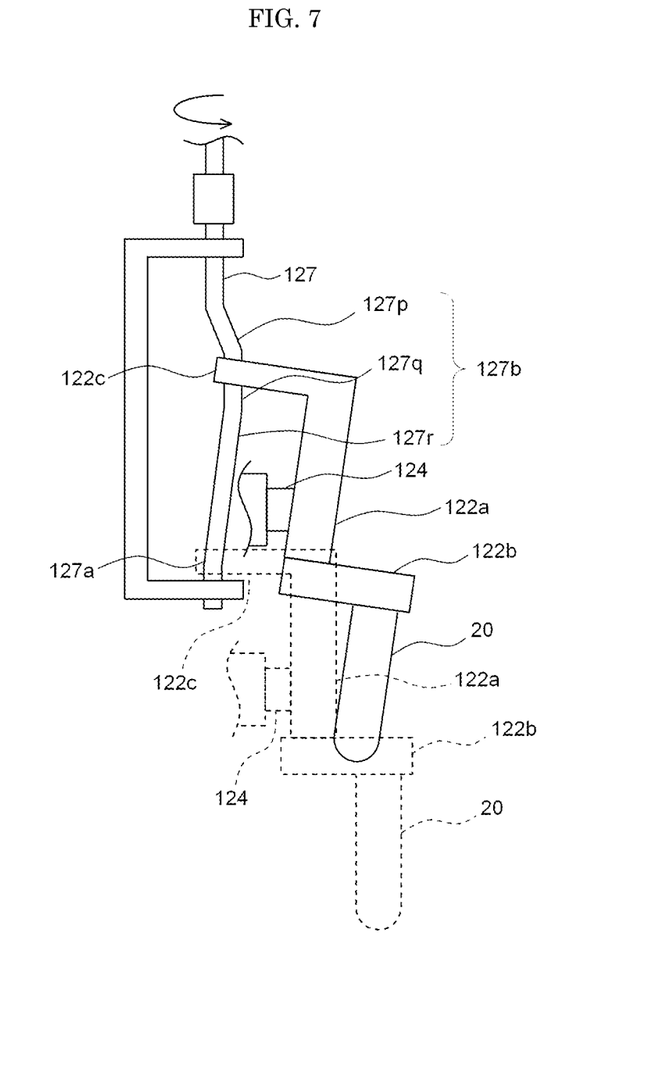
FIG. 7 is a schematic view illustrating the operation of the agitation apparatus of the embodiment.

FIG. 7 is a schematic view illustrating the operation of the agitating apparatus 12. When the catcher 122 is disposed at the second position, the through hole provided in the connecting part 122c of the catcher 122 is positioned at the linear part 127q of the rotating shaft 127. When the agitating apparatus 12 performs the agitating operation, the motor 126 is actuated in the condition to rotate the rotating shaft 127. Hence, the eccentric part 127b rotates eccentrically and the connecting part 122c disposed at the linear part 127q rotates together with the eccentric part 127q around the center of rotation of the rotating shaft. That is, the inner wall of the through hole of the connecting part 122c periodically displaces (oscillates) the catcher 122 via the contact with the linear part 127q of the rotating shaft 127. At this time the catcher 122 is supported by the rubber support 124, and the catcher 122 is displaced (oscillated) by pivoting on the rubber support 124 within the tolerance range of the elastic force of the rubber support 124. As a result, the periodic operation of the catcher 122 is repeated continuously through the continued operation of the motor 126, and hence the reaction container 20 held by the catcher 122 is oscillated so as to agitate and mix the sample and reagent within the reaction container 20.

After the sample and reagent are agitated in the reaction container 20, the reaction container 20 is again inserted in the holder of the measuring unit 8. At this time, the container transporting unit 10 is moved in the X direction and the Y direction to move the catcher 122 toward the reaction container supplier 7. With the catcher 122 positioned above one holder of the measuring unit 8, the motor 125 is actuated and the elevator block 123 and the catcher 122 integratedly descend as a unit so that the reaction container 20 is inserted into the hole. After the reaction container 20 is inserted in the holder, the motor 14 is actuated to move backward within the frame 11. The gripping part 122b and the flange 21 of the reaction container 20 thus disengage and the reaction container 20 is removed from the catcher 122.

Since the catcher 122 is supported by a plurality of members (rubber support 124 and rotating shaft 127) as described above, the positional accuracy of the catcher 122 is adequately ensured and poor holding of the reaction container 20 is avoided when the catcher 122 is moved to the container supplying position of the reaction container supplier 7. Since the catcher 122 can be oscillated by the rotation of the rotating shaft 127, the rotating shaft 127 has the effect of ensuring the positional accuracy of the catcher 122 and the effect of oscillating the catcher 122. Therefore, the liquid within the reaction container 20 can be agitated and poor holding of the reaction container 20 can be avoided by this simple construction. Note that since the sample and reagent can be dispensed to the reaction container 20 and the catcher 122 can be supported at two points by the rubber support 124 and the positioning unit 127a of the rotating shaft 127, positional accuracy of the catcher 122 can be adequately ensured and inadequate agitation of the sample and reagent is avoided.

Since the catcher 122 is normally supported by the rotating shaft 127 and the positioning part 127q when the catcher 122 grips the reaction container 20 and when the sample and reagent are dispensed, the catcher 122, the orientation of the catcher 122 relative to the base 121 is constant, thus readily ensuring the positional accuracy of the catcher 122.

The function of agitating the liquid within the reaction container 20 and the function of gripping the reaction container 20 are readily switchable insofar as the connecting part 122c of the catcher 122 is positioned at the eccentric part 127b when the reaction container 20 is oscillated and insofar as the catcher 122 is positioned at the positioning part 127a when the reaction container 20 is gripped. The function of agitating the liquid within the reaction container 20 and the function of gripping the reaction container 20 are readily switchable by simply changing the position of the catcher 122 along the rotating shaft 127.

The amount of displacement (distance) from the center of rotation of the rotating shaft 127 to the connection area of the catcher 122 and the rotating shaft can be changed and the oscillation radius (amplitude of oscillation) of the catcher 122 can be easily changed by moving the catcher 122 along the rotating shaft 127. Therefore, the oscillation radius of the catcher 122 can be easily changed without changing the output of the motor 126. Spilling of the liquid from the reaction container 20 can be prevented by changing the oscillation radius of the catcher 122 according to the amount of liquid in the reaction container 20. Note that since a step motor is used as the motor 126, the number of rotations of the motor 126 can be controlled and the oscillation speed of the catcher 122 is easily changeable.

Since the leverage point of the connection part 122c is provided on the opposite side of the action point of the gripping part 122b sandwiching the pivot point of the base 122a when the reaction container 20 is oscillated, the amount of displacement of the gripping part 122b can be suitably adjusted when the motor 126 is actuated by appropriately setting the distance between the base 122a and the gripping part 122b and the distance between the base 122a and the connecting part 122c. Since the base 122a and the connecting part 122c are fixed relative to the base 121 when the reaction container 20 is gripped, the positional accuracy of the catcher 122 can be readily ensured by fixing the gripping part 122b relative to the base 121.

Other Embodiments

Figure 8A:
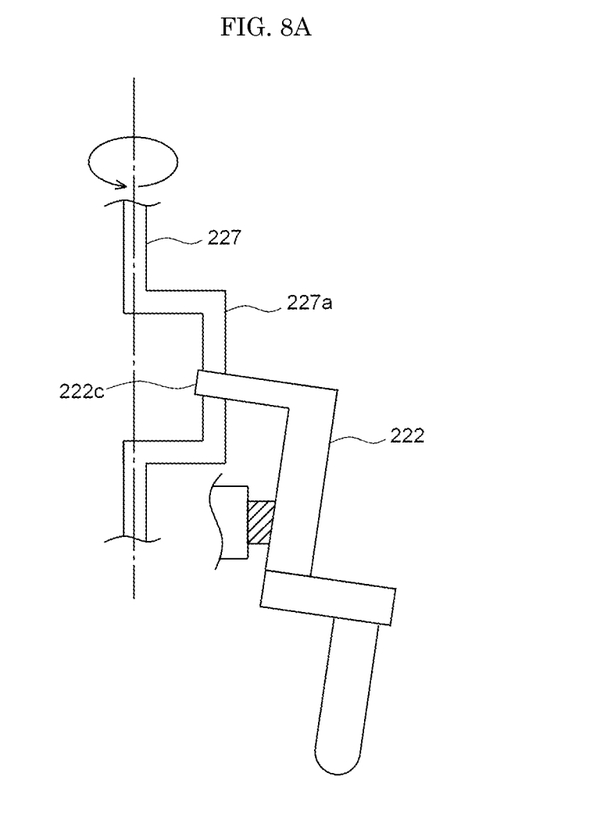
FIG. 8A is a schematic left side view of another example of an agitation apparatus.

Note that although the above embodiment is described as having a structure wherein the rotating shaft 127 is provided with a linear part 127a and eccentric part 127b, and the eccentric part 127b is provided with a first incline 127p, linear part 127q, and second incline 127r, the present invention is not limited to this configuration. As shown in FIG. 8A, for example, a rotating shaft 227 which is bent in a square crank shape may be provided, and a connecting part 222c of a catcher 222 may be connected at the crank part 227a separated from the center of rotation of the rotating shaft 227. Hence, the crank part 227a rotates eccentrically via the rotating of the rotating shaft 227, and this eccentric rotation oscillates the reaction container gripped in the catcher 222.

Figure 8B:
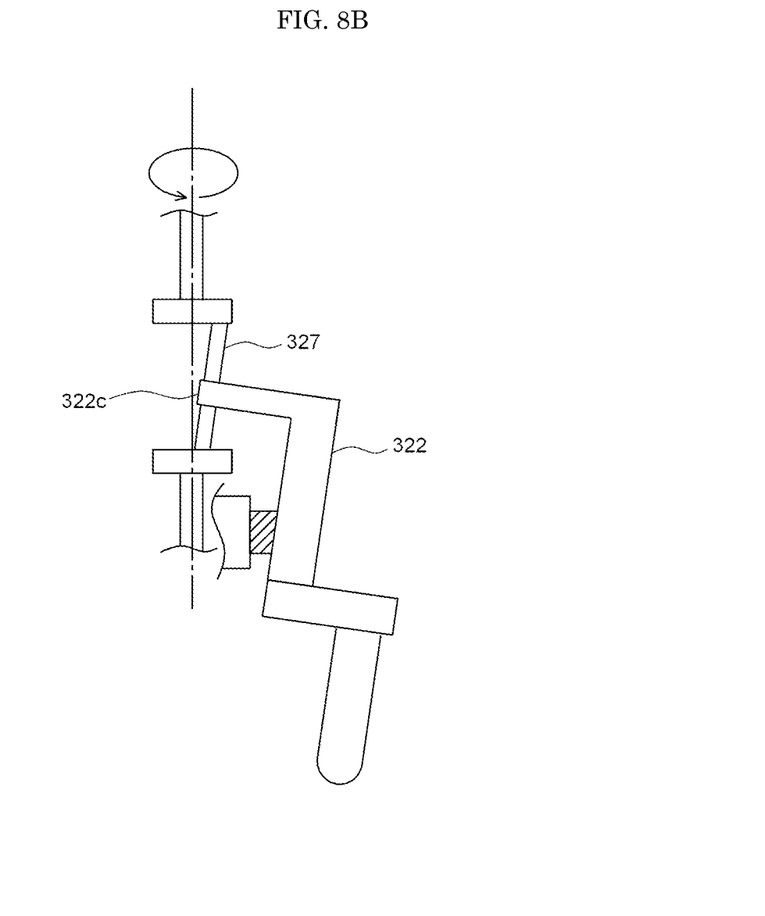
FIG. 8B is a schematic left side view of another example of an agitation apparatus.

The structure shown in FIG. 8B shows a rotating shaft 327 which is inclined relative to the center of rotation may be provided, with a connecting part 322c of the catcher 322 being connected at a suitable location of the rotating shaft 327. In this way the eccentric rotation of the rotating shaft 327 oscillates the reaction container gripped by the catcher 322.

Figure 8C:
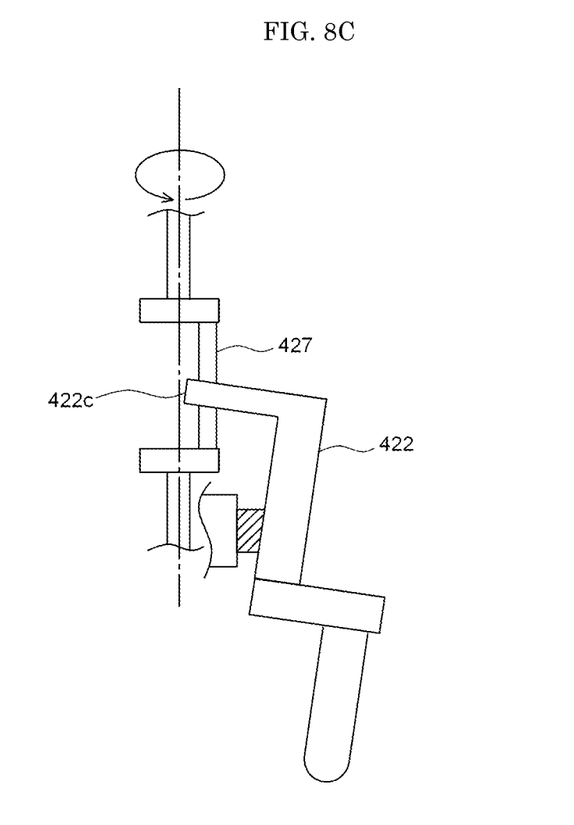
FIG. 8C is a schematic left side view of another example of an agitation apparatus.

The structure shown in FIG. 8C shows a rotating shaft 427 which is parallel to the axial direction of the center of rotation at a predetermined distance is provided, and a connecting part 422c of the catcher 422 is connected at the rotating shaft 427. In this way the eccentric rotation of the rotating shaft 427 oscillates the reaction container gripped by the catcher 422.

In the embodiments shown in FIGS. 8A through 8C, the crank 227a, rotating shafts 327 and 427 are preferably stopped at a fixed position (rotational angle) when the empty catcher first grips a reaction container. In this way the catcher can be supported at a constant position (orientation) by the crank 227a and rotating shafts 327 and 427 when the empty catcher first grips a reaction container, thus ensuring sufficient positional accuracy.

Figure 9:
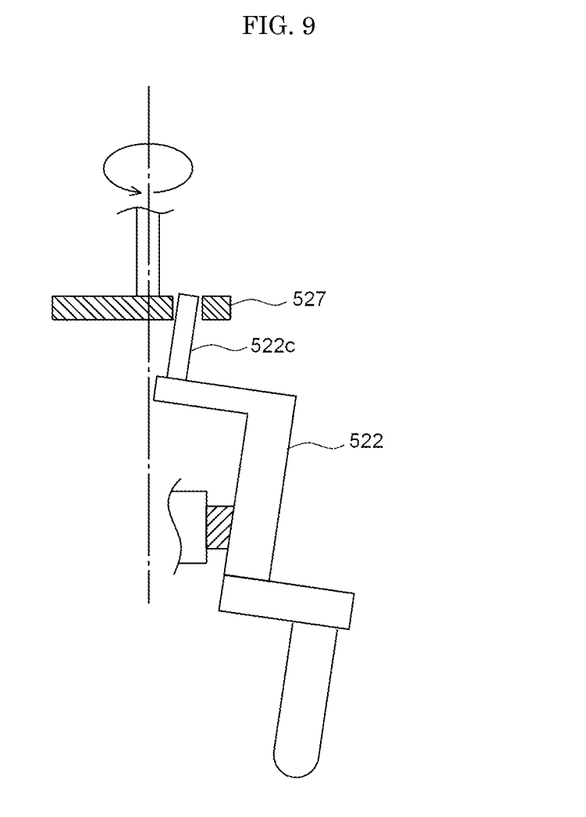
FIG. 9 is a schematic left side view of another example of an agitation apparatus.

Although the above embodiments are described in terms of structures in which a through hole is provided in the catcher 122, and the catcher 122 and rotating shaft 127 are connected by having the rotating shaft 127 pass through the through hole, the present invention is not limited to this configuration. For example, a disk 527 which rotates in conjunction with the rotation of a motor may be provided, and a hole may be provided at a position separated from the center of a disk 527, as shown in FIG. 9. A rod-like part 522c is provided at part of the catcher 522, and this rod 522c is inserted in the hole of the disk 527. When the motor rotates, the disk 527 rotates and the hole provided in the disk 527 then rotates eccentrically. Since the rod 522c connected to the hole also rotates eccentrically, the reaction container gripped in the catcher 522 is oscillated.

A rotating shaft 127 also may be connected to the output shaft of the motor 126 without providing the power transmitting mechanism 130 which includes the transmission belt 130a and pulleys 130b and 130c. The connecting part 122c of the catcher 122 also may be connected to the output shaft of the motor 126 while configuring the output shaft of the motor 126 in the same shape as the rotating shaft 127.

Although the above embodiment have been described in terms of a structure in which the catcher 122 is supported by the rubber support 124, the present invention is not limited to this configuration. The rubber elastic body is unnecessary insofar as the catcher 122 is supported and the catcher 122 can be displaced (oscillated) in a predetermined range; for example, the catcher 122 may be supported by a universal joint.

The catcher 122 also may be oscillated by a method other than the rotation of the rotating shaft. For example, the catcher may be oscillated by connecting the catcher to a solenoid which reciprocates linearly to transmit the power of the solenoid to the catcher.

An eccentric cam also may be mounted on the rotating shaft, and the eccentric cam connected to the catcher. In this case the eccentric cam rotates eccentrically via the rotation of the rotating shaft to oscillate the catcher.

Although the reaction container supplier 7 is configured to automatically supply the reaction container, the reaction container also may be manually loaded in the reaction container supplier to supply the reaction container to the catcher 122.

Although the sample analyzer 1 is a blood coagulation measuring apparatus in the above embodiment, the present invention is not limited to this configuration. For example, the agitating apparatus of the above embodiments is also applicable to other sample analyzers, such as biochemical analyzers, immunoanalyzers and the like.

The agitating apparatus and analyzer of the present invention may also be used as an agitating apparatus for agitating liquid in a container and a sample analyzer provided with same.

What is claimed is:

1. An analyzer comprising:
    a container storage area;
    an agitator configured to agitate liquid in a container; and
    a measurement unit configured to perform a measurement using the liquid agitated by the agitator,
    wherein the agitator is movable between the container storage area and the measurement unit, and comprises:
        a motor;
        a container catcher; and
        a rotating shaft comprising an eccentric part formed by a bend in the rotating shaft which rotates in conjunction with the motor and is coupled to the container catcher by a supporting member.

2. The analyzer of claim 1, wherein the container catcher is movable to a container catching position adjacent to the container storage area.

3. The analyzer of claim 1, wherein the eccentric part supports the container catcher when the container catcher translates along the eccentric part, and
the motor is configured to oscillate the rotating shaft.

4. The analyzer of claim 3, wherein the container catcher is supported by the rotating shaft, and the container catcher is movable along the eccentric part.

5. The analyzer of claim 3, wherein the rotating shaft is inserted into a through hole or a concavity defined by the container catcher; and
the container catcher is configured to oscillate when the eccentric part is in contact with the inner wall of the through hole or the concavity in conjunction with the rotating shaft.

6. The analyzer of claim 3, wherein the eccentric part comprises an inclined portion inclined relative to a center of rotation of the rotating shaft.

7. The analyzer of claim 3, wherein the eccentric part comprises a linear portion parallel to a center of rotation of the rotating shaft.

8. The analyzer of claim 1, wherein the supporting member is an elastic member.

9. The analyzer of claim 1, wherein the agitator further comprises:
a pulley connected to the rotating shaft; and
a transmission belt connected to the motor and the pulley.

10. The analyzer of claim 1 further comprising:
a sample dispenser; and
a reagent dispenser.

11. An analyzer comprising:
a container storage area;
an agitator configured to agitate liquid in a container; and
a measurement unit configured to perform a measurement using the liquid agitated by the agitator,
wherein the agitating unit is movable between the container storage area and the measurement unit, and comprises:
a motor;
a container catcher; and
a rotating shaft comprising an eccentric part formed by a bend in the rotating shaft which rotates in conjunction with the motor and is coupled to the container catcher by a supporting member,
wherein the rotating shaft is rotated by the motor to oscillate the container.

12. The agitating apparatus of claim 11, wherein
the eccentric part eccentrically oscillates in conjunction with the motor.

13. The agitating apparatus of claim 11, further comprising a flexible supporting member connecting the rotating shaft to the container catcher.

* * * * *